United States Patent [19]
Mann

[11] Patent Number: 5,941,243
[45] Date of Patent: Aug. 24, 1999

[54] APPARATUS AND METHOD FOR ETHYL CHLORIDE TOPICAL ANESTHESIA

[76] Inventor: Richard H. Mann, 258 SE. 6th Ave., Delray Beach, Fla. 33483

[21] Appl. No.: 08/953,826

[22] Filed: Oct. 16, 1997

[51] Int. Cl.⁶ .................................................. A61M 15/00
[52] U.S. Cl. .............................. 128/203.12; 128/200.23; 514/757
[58] Field of Search ........................... 128/203.12, 200.23

[56] References Cited

U.S. PATENT DOCUMENTS 4,216,233   8/1980   Stein ........................................ 424/350

OTHER PUBLICATIONS

Hawley's Condensed Chemical Dictionary, ISBN 0–422–28097–1, p. 482, 1987.

Primary Examiner—John G. Weiss
Assistant Examiner—Todd Martin
Attorney, Agent, or Firm—Alvin S. Blum

[57] ABSTRACT

Apparatus for topical anesthesia by evaporative cooling with ethyl chloride (chloroethane) constitutes a container holding liquid ethyl chloride under pressure. A valve attached to the container hermetically seals the container in a first mode of operation. A second mode of operation of the valve is affected by finger pressure to emit a divergent fluid stream of ethyl chloride. The method of topical anesthesia using the apparatus constitutes positioning the surface area to be anesthetized at a distance from a divergent fluid stream of ethyl chloride such that a substantial portion of that area will subtend the divergent stream to provide faster and more uniform cooling than the non-divergent ethyl chloride stream of the prior art.

2 Claims, 1 Drawing Sheet

APPARATUS AND METHOD FOR ETHYL CHLORIDE TOPICAL ANESTHESIA

BACKGROUND OF THE INVENTION

This invention relates to topical anesthesia, and more particularly to apparatus and method for inducing anesthesia of a body surface by the rapid cooling action of ethyl chloride.

Ethyl chloride, also known as chloroethane, has a boiling point of 12.27° C. Wohen applied as a liquid to skin having a temperature of about 37° C., it boils off rapidly. The skin temperature is rapidly reduced as heat from the skin is transferred to the liquid and converted to heat of vaporization as the liquid is converted to gas. The skin becomes so cold that it is anesthetized.

This phenomenon has been employed for topical anesthesia for at least a century. Because of the high vapor pressure of the liquid at room temperature, it is stored in a pressure resistant container. The container is fitted with a spring loaded valve. When the valve is depressed a jet or straight stream of the liquid is emitted. This stream is directed to the skin surface to be anesthetized. When the stream hits the surface, it spreads out on the surface while it boils. The point of impingement of the stream is flushed with fresh liquid while the perimeter of the fluid pool is boiling. Consequently, the surface wet by the liquid is not uniformly cooled. The user may move the stream around on the skin surface to try to provide more uniform or larger cooling action. While this apparatus and method have been in use for at least about a century, a means of more uniform cooling and better adjustment of the area cooled would be helpful.

SUMMARY OF THE INVENTION

The apparatus of the invention comprises a pressurized container of ethyl chloride equipped with a valve means for hermetically sealing the ethyl chloride in a first mode of operation. The valve is actuated by finger pressure to a second mode of operation in which the ethyl chloride is emitted in a divergent fluid stream. Since the stream is divergent, the apparatus may be positioned at a distance from the body surface such that at least a substantial portion of the area to be anesthetized will be wet directly by the fluid stream. By more uniformly applying the fluid to the area at the same time, more rapid and uniform anesthesia is achieved by evaporative cooling of the ethyl chloride.

The method of topical anesthesia of the invention comprises spraying the surface area with the divergent stream of ethyl chloride while holding the valve far enough away that at least a substantial portion of area to be anesthetized is wetted at the same time.

These and other objects, advantages and features of the invention will become more apparent when the detailed description is studied in conjunction with the drawings.

DETAILED DESCRIPTION OF PREFERRED EMBODIMENTS

Figures 1, 2:
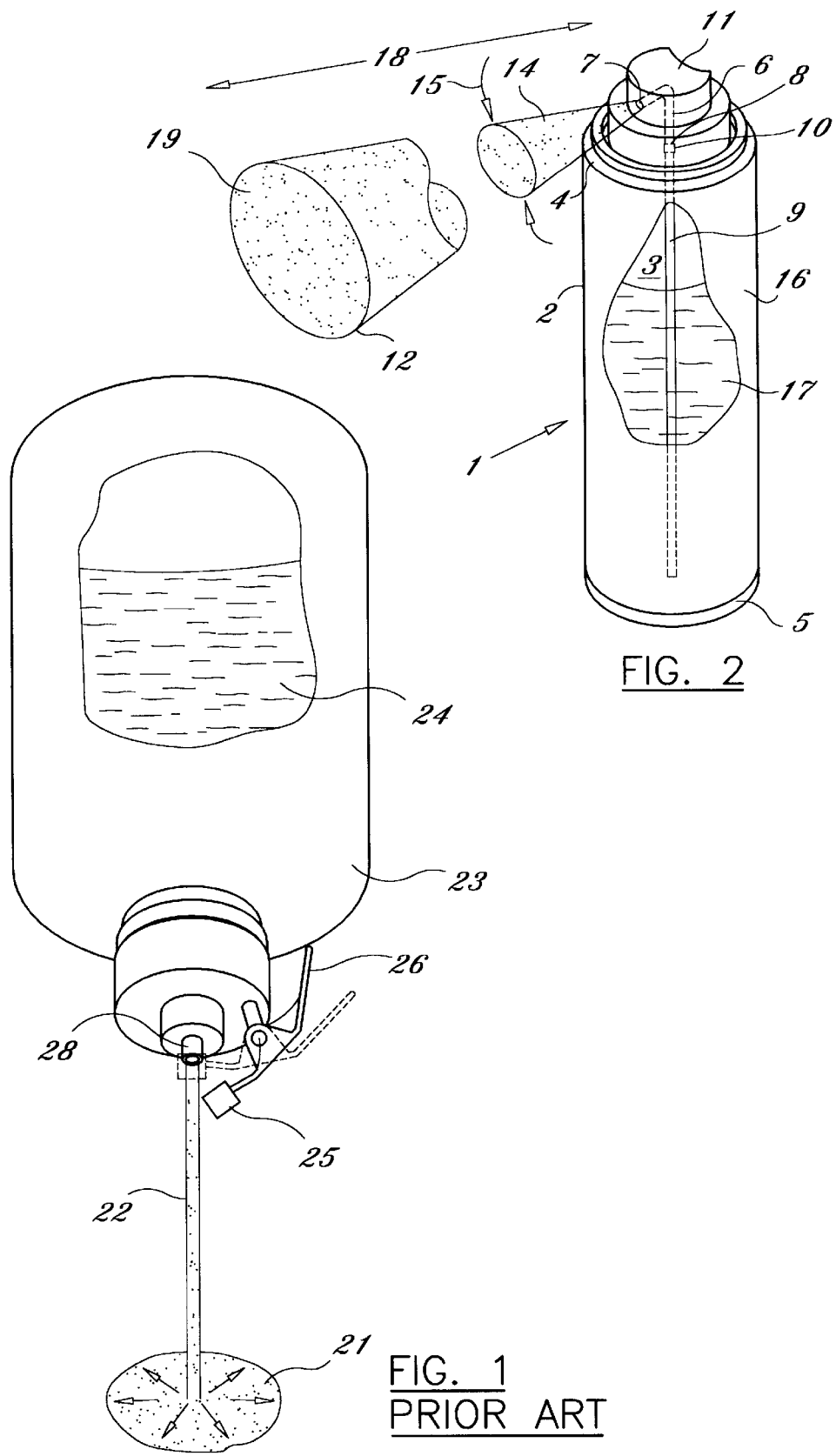
FIG. 1 is a perspective view of apparatus of the prior art for topical anesthesia with ethyl chloride.
FIG. 2 is a perspective view of apparatus of the invention for topical anesthesia with ethyl chloride.

Referring now first to FIG. 1, the topical anesthesia apparatus and method that has been in use for about a century comprises a can or bottle 23 containing ethyl chloride 24 at room temperature. A tube or passage 28 communicates with the liquid 24. A spring loaded valve 25 closes off and hermetically seals the container. When valve actuator 26 is depressed, a non-divergent stream 22 of the liquid is forced from the valve by the pressure in the container. The container is not provided with a syphon tube and must be used inverted as shown to spray liquid in a straight, substantially non-divergent, stream. An advantage of the straight non-divergent nature of the emitted stream 22 is that distance of the container from the surface is not critical. The area of the stream subtended by the skin surface is independent of the distance. In order to cool the area 21, the stream may be moved about that area. A disadvantage is that the impinging stream of liquid is not very cold. That stream will be warming the surface it first touches. This phenomenon makes it difficult to cool the area uniformly to anesthetizing temperature.

Referring now to FIG. 2, the apparatus 1 of the invention comprises a container 16 having walls 2 enclosing a chamber 3, with upper end wall 4 and lower end wall 5. A tubular passage 6 extends through upper end wall 4, terminating in a first passage end 7 that is at the end of syphon tube 9. The chamber 3 contains a liquid that consists substantially of ethyl chloride 17. A valve 10 at a second end 8 of the passage 6 hermetically seals chamber 3 in a first mode of operation by means well known in the art. When valve actuator 11 is depressed by finger pressure, the valve assumes a second mode of operation, causing a divergent fluid stream 14 of ethyl chloride to be forcefully emitted by the vapor pressure of the liquid in the container. The stream has a generally conical configuration having a cone angle 15 of between about five and thirty-five degrees. As the stream diverges, it breaks up into droplets with great surface to volume ratio. Consequently, they cool by evaporation before hitting the body surface. The cold droplets on the skin then evaporate to provide further cooling of the skin. In the method of the invention, the apparatus 1 is positioned at a distance 18 from the surface 12 to be anesthetized such that the area 19 of the conical stream subtended by the skin surface is equal to a substantial portion of the area to be anesthetized. Since there is no concentrated room temperature jet of fluid to warm some of the area, more rapid and uniform evaporative cooling and anesthesia is produced.

In an alternative embodiment (not shown) the syphon tube may be omitted and the apparatus used by inverting the container.

Containers and valves, both with and without syphon tubes, that are suitable for this invention are well known in the art.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

What is claimed is:

1. A method for inducing topical anesthesia of a body skin are comprising: the steps of:

A) providing a pressurized container having walls enclosing a chamber containing a liquid consisting of ethyl chloride, the container being equipped with a valve means for emitting a divergent conical stream of liquid upon actuation of the valve means;

B) positioning the valve means at a distance from a skin area to be anesthetized such that the divergent fluid stream will contact the skin area substantially equal to the area to be anesthetized; and C) actuating the valve means while causing the fluid stream to impinge upon the area, thereby uniformly reducing the temperature of the skin area exposed to the ethyl chloride by evaporative cooling to induce anesthesia.

2. The method of claim 1, in which the fluid stream emitted is substantially conical, having a cone angle of between about five degrees and thirty five degrees.

* * * * *

UNITED STATES PATENT AND TRADEMARK OFFICE
CERTIFICATE OF CORRECTION

PATENT NO. : 5,941,243 Page 1 of 1
APPLICATION NO. : 08/953826
DATED : August 24, 1999
INVENTOR(S) : Richard H. Mann It is certified that error appears in the above-identified patent and that said Letters Patent is hereby corrected as shown below:

Column 1, line 11, delete "Wohen". In its place insert --When--.

Signed and Sealed this

Eighteenth Day of July, 2006

JON W. DUDAS
*Director of the United States Patent and Trademark Office*